United States Patent
Ko et al.

(10) Patent No.: US 10,458,958 B1
(45) Date of Patent: Oct. 29, 2019

(54) ULTRASONIC THROUGH-THICKNESS MODULUS EVALUATION OF MATERIALS

(71) Applicant: Government of the United States, as Represented by the Secretary of the Air Force, Wright-Patterson AFB, OH (US)

(72) Inventors: Ray T. Ko, Dublin, OH (US); Ming-Yung Chen, Beavercreek, OH (US)

(73) Assignee: United States of America as Represented by the Secretary of the Air Force, Wright-Patterson AFB, OH (US)

( * ) Notice: Subject to any disclaimer, the term of this patent is extended or adjusted under 35 U.S.C. 154(b) by 152 days.

(21) Appl. No.: 15/876,250

(22) Filed: Jan. 22, 2018

Related U.S. Application Data

(60) Provisional application No. 62/449,667, filed on Jan. 24, 2017.

(51) Int. Cl.
*G01N 29/04* (2006.01)
*G01N 29/07* (2006.01)
*G01N 29/28* (2006.01)

(52) U.S. Cl.
CPC .......... *G01N 29/28* (2013.01); *G01N 29/041* (2013.01); *G01N 29/07* (2013.01);
(Continued)

(58) Field of Classification Search
CPC ...... G01N 29/28; G01N 29/07; G01N 29/041; G01N 2291/02854; G01N 2291/0427; G01N 2291/0231; G01N 2291/0237
(Continued)

(56) References Cited

U.S. PATENT DOCUMENTS 3,012,211 A * 12/1961 Mason ................... H03H 9/125
333/149
3,529,465 A * 9/1970 Eisenmenger ........... G01N 3/38
73/577
(Continued)

FOREIGN PATENT DOCUMENTS

IN 200100699 * 1/2009

*Primary Examiner* — Jacques M Saint Surin
(74) *Attorney, Agent, or Firm* — AFMCLO/JAZ; Timothy Barlow

(57) ABSTRACT

An apparatus for performing non-destructive evaluation of the through-thickness modulus of a specimen comprises: a first low-frequency ultrasonic longitudinal wave transducer configured to be coupled to a first surface of a specimen to be tested with a first delay line, the specimen having a layer of fibers perpendicular to the first surface and the second surface; a second low-frequency ultrasonic longitudinal wave transducer configured to be coupled to a second surface of the specimen with a second delay line, the second contact point at a predetermined distance from the first contact point, the predetermined distance corresponding to the distance between the first surface and second surface, wherein the first low-frequency ultrasonic longitudinal wave transducer is configured to transmit a guided wave into the specimen in plane with layer of fibers, and the second low-frequency ultrasonic longitudinal wave transducer is configured to receive the guided wave from the first ultrasonic longitudinal wave transducer; and a first high-frequency longitudinal wave transducer and a second high-frequency longitudinal wave transducer configured to generate and receive both in-plane and out-of-plane ultrasonic signals in the specimen.

10 Claims, 16 Drawing Sheets

(52) U.S. Cl.
CPC ............... *G01N 2291/011* (2013.01); *G01N 2291/0231* (2013.01); *G01N 2291/0237* (2013.01); *G01N 2291/02854* (2013.01); *G01N 2291/0427* (2013.01)

(58) Field of Classification Search
USPC .......................................................... 73/597
See application file for complete search history.

(56) References Cited

U.S. PATENT DOCUMENTS

| | | | | | |
|---|---|---|---|---|---|
| 3,789,328 | A | * | 1/1974 | Putnam | H03H 9/30 333/141 |
| 4,868,357 | A | * | 9/1989 | Serikawa | H05B 6/6411 219/706 |
| 5,691,476 | A | * | 11/1997 | Madaras | A61B 8/4281 73/625 |
| 2003/0221489 | A1 | * | 12/2003 | Koo | G01H 5/00 73/597 |
| 2004/0255678 | A1 | * | 12/2004 | Nagashima | G01N 29/221 73/620 |
| 2014/0316719 | A1 | * | 10/2014 | Lanza di Scalea | G01M 5/0025 702/42 |

* cited by examiner

ULTRASONIC THROUGH-THICKNESS MODULUS EVALUATION OF MATERIALS

Pursuant to 37 C.F.R. § 1.78(a)(4), this application claims the benefit of and priority to prior filed Provisional Application Ser. No. 62/449,667, filed Jan. 24, 2017, which is expressly incorporated herein by reference.

RIGHTS OF THE GOVERNMENT

The invention described herein may be manufactured and used by or for the Government of the United States for all governmental purposes without the payment of any royalty.

FIELD OF THE INVENTION

The present invention relates generally to the non-destructive evaluation of materials and, more particularly, to ultrasonic testing apparatuses and methods.

BACKGROUND OF THE INVENTION

Ceramic matrix composites (CMC) have an advantage over polymeric matrix composites because of their high-temperature performance. The mechanical properties of these composites are critical for both material researchers and modeling engineers to evaluate material performance. One of the properties of interest is the through-thickness modulus of the composites. For thick composites, i.e., about 20 mm thickness, this modulus may be estimated by mechanical testing. However, most CMCs are thin, i.e., about 2 mm; thus measuring through-thickness properties by conventional mechanical methods is difficult and results in destruction of the specimen. Other mechanical test methods have been proposed, such as stacking multiple CMC panels together and testing them in compression.

Ultrasonic non-destructive evaluation (NDE) may provide the ability to measure through-thickness modulus needed for modeling support. However, typical ultrasonic studies on composites are conducted by immersing the specimen in a water tank and often requires a complicated inversion process to derive elastic constants from the ultrasonic amplitude data. For non-immersion tests or contact ultrasonic methods, elastic constants can be measured directly by the ultrasonic bulk wave velocity, but a disadvantage of this approach is that it requires multiple specimens of different orientations. Modulus evaluations of materials, if feasible, are typically performed in a tensile test machine which requires destruction of the specimen from which the material is received. Accordingly, such materials and the specimen are no longer able to be used.

SUMMARY OF THE INVENTION

The present invention overcomes the foregoing problems and other shortcomings, drawbacks, and challenges of non-destructive testing of materials. While the invention will be described in connection with certain embodiments, it will be understood that the invention is not limited to these embodiments. To the contrary, this invention includes all alternatives, modifications, and equivalents as may be included within the spirit and scope of the present invention.

This work teaches a nondestructive approach which employs three ultrasonic measurements combined with known values of the Poisson's ratio and the density for the specimen, e.g. CMC material, which may be used to determine the through-thickness modulus of thin, e.g. about 5 mm or less, cross-ply composites with orthotropic symmetry. Three of the four elastic constants needed for determining through-thickness modulus values may be evaluated by the disclosed contact ultrasonic technique. These measurements may include two high frequency measurements, e.g. 15 MHz or greater, in two orientations and a low frequency measurement, e.g. 0.5 MHz or less, in the in-plane direction. The low frequency measurement may be based on guided waves of the lowest symmetric mode. The in-plane Poisson's ratio may be obtained by mechanical means or through ultrasonic measurements. The mechanical testing of the Poisson's ratio may be conducted at a very low stress level (i.e., about 25-75 MPa); accordingly, this type of measurement may be considered as nondestructive in nature. By combining results from three ultrasonic measurements along with the density and the Poisson's ratio data for the specimen, the through-thickness modulus may be determined. This invention documents the experimental test setup and procedure for the evaluation of the through-thickness modulus, and the basis that relates ultrasonic velocity with the through-thickness modulus.

This invention is a major improvement in the technology of through-thickness (out-of-plane) modulus testing of thin materials. No known methods have been disclosed for making a through-thickness modulus evaluation using ultrasonic contact measurements on thin composites. This disclosed apparatuses and methods demonstrate the use of an ultrasonic approach in the evaluation of the through-thickness modulus in specimens, e.g. thin cross-ply ceramic matrix composites (CMC). The determination of modulus estimates through the thickness direction of a CMC is often considered challenging by mechanical testing because of the small (thin) dimension. i.e., 2 mm. Anisotropy may also add to the complexity in estimating this modulus. Herein, a unique approach is presented which employs both guided waves as well as bulk ultrasonic waves in order to evaluate the through-thickness modulus of thin cross-ply composites with orthotropic symmetry. The through-thickness modulus of this type of CMC may be simplified to be dependent on four elastic constants. Three of these constants may be evaluated using ultrasonic velocity measurements while the fourth elastic constant may be derived using these constants as well as the in-plane Poisson's ratio. To the best of our knowledge, similar methods and apparatuses have not been reported previously.

An apparatus for performing non-destructive evaluation of the through-thickness modulus of a specimen comprises: a first low-frequency ultrasonic longitudinal wave transducer configured to be coupled to a first surface of a specimen to be tested with a first delay line, the specimen having a layer of fibers perpendicular to the first surface and the second surface; a second low-frequency ultrasonic longitudinal wave transducer configured to be coupled to a second surface of the specimen with a second delay line, the second contact point at a predetermined distance from the first contact point, the predetermined distance corresponding to the distance between the first surface and second surface, wherein the first low-frequency ultrasonic longitudinal wave transducer is configured to transmit a guided wave into the specimen in plane with layer of fibers, and the second low-frequency ultrasonic longitudinal wave transducer is configured to receive the guided wave from the first ultrasonic longitudinal wave transducer; and a first high-frequency longitudinal wave transducer and a second high-frequency longitudinal wave transducer configured to generate and receive both in-plane and out-of-plane ultrasonic signals in the specimen.

This arrangement makes it possible to determine the through-thickness modulus of the specimen without destroying the specimen.

According to another embodiment of the invention, the first low-frequency ultrasonic longitudinal wave transducer and the second ultrasonic longitudinal wave transducer are configured to operate at or below 0.5 MHz (500 kHz).

This arrangement may ensure that the modulus measurement stays in the low frequency asymptote region of the lowest symmetric mode for an in-plane modulus evaluation on a thin specimen. The use of a longitudinal wave contact method on the same side of a thin specimen may induce the lowest symmetric mode of a Lamb wave, which makes it possible to perform nondestructive evaluation of specimens.

According to a further embodiment of the invention, the apparatus for performing nondestructive evaluation of the through-thickness modulus of a specimen further comprises a dry couplant between the first and second low-frequency ultrasonic longitudinal wave transducers and the specimen.

According to another embodiment of the invention, the dry couplant comprises a membrane between the first and second low-frequency ultrasonic longitudinal wave transducers and the specimen.

Advantageously, ultrasonic signals may be passed into a specimen without any liquid or gel ultrasound couplant. This provides an advantage over traditional ultrasonic bulk waves or guided-wave measurements which usually require ultrasonic gel or water immersion because the dry contact ultrasonic approach reduces or eliminates the risk of contaminating the materials, which may happen during immersion or with a liquid couplant. The dry couplant also makes it possible to operate the ultrasonic longitudinal wave transducers in a low frequency range, e.g. at or below 0.5 MHz (at or below 500 kHz).

According to a further embodiment of the invention, the first high-frequency ultrasonic longitudinal wave transducer and the second high-frequency ultrasonic longitudinal wave transducer are configured to operate at or above 15 MHz.

This arrangement permits ultrasonic waves to be passed into the specimen, both in-plane with the layer of fibers and perpendicular to the plane of the fibers, i.e. through-thickness. A thin film of water may be the only couplant needed for coupling the high-frequency transducers to the specimen.

According to another embodiment of the invention, the dry couplant is a nitrile rubber, vinyl, or polyester membrane.

Ultrasonic waves may be passed into a specimen without any liquid or gel ultrasound couplant. This provides an advantage over traditional ultrasonic bulk waves or guided-wave measurements which usually require ultrasonic gel or water immersion because the dry contact ultrasonic approach reduces or eliminates the risk of contaminating the materials, which may happen during immersion or with a liquid couplant. The dry couplant also makes it possible to operate the ultrasonic longitudinal wave transducers in a low frequency range, e.g. at or below 0.5 MHz (at or below 500 kHz).

According to a further embodiment of the invention, a method for performing nondestructive evaluation of the through-thickness modulus of a specimen comprises: coupling a first low-frequency ultrasonic wave transducer to a first surface of a specimen to be tested with a first delay line; coupling a second low-frequency ultrasonic wave transducer to a second surface of the specimen at a predetermined distance from the first low-frequency ultrasonic longitudinal wave transducer with a second delay line, the specimen having a layer of fibers oriented perpendicular to the first surface and the second surface, the predetermined distance corresponding to the distance between the first surface and the second surface; transmitting a guided wave from the first low-frequency ultrasonic wave transducer into the specimen at the first surface via the first delay line; receiving the guided wave by the second low-frequency ultrasonic wave transducer at the second surface via the second delay line, wherein the first low-frequency ultrasonic wave transducer is configured to transmit a wave into the specimen, and the second low-frequency ultrasonic wave transducer is configured to receive the wave from the first low-frequency ultrasonic wave transducer; and coupling a first high-frequency longitudinal wave transducer at the first surface to transmit a first high-frequency ultrasonic wave into the specimen; coupling a second high-frequency longitudinal wave transducer at the second surface to receive the first high-frequency ultrasonic wave; coupling the first high-frequency longitudinal wave transducer at a third surface to transmit a second high-frequency ultrasonic wave into the specimen; coupling the second high-frequency longitudinal wave transducer at a fourth surface to receive the second high-frequency ultrasonic wave, the third surface and further surface being perpendicular to the first surface and second surface.

This arrangement makes it possible to determine the through-thickness modulus of the specimen without destroying or contaminating the specimen.

According to another embodiment of the invention, the method for performing nondestructive evaluation of the through-thickness modulus of a specimen further comprises operating the first low-frequency ultrasonic wave transducer and the second low-frequency ultrasonic wave transducer at or below 0.5 MHz (500 kHz).

This arrangement may ensure that the modulus measurement stays in the low frequency asymptote region of the lowest symmetric mode for an in-plane modulus evaluation on a thin specimen. The use of a longitudinal wave contact method on the same side of a thin specimen may induce the lowest symmetric mode of a Lamb wave, which makes it possible to perform nondestructive evaluation of specimens.

According to a further embodiment of the invention, the method for performing nondestructive evaluation of the through-thickness modulus of a specimen of claim 8, further comprises operating the first high-frequency ultrasonic wave transducer and the second high-frequency ultrasonic wave transducer at or above 15 MHz.

This arrangement permits ultrasonic waves to be passed into the specimen, both in-plane with the layer of fibers and perpendicular to the plane of the fibers, i.e. through-thickness. A thin film of water may be the only couplant needed for coupling the high-frequency transducers to the specimen.

According to another embodiment of the invention, the method for performing nondestructive evaluation of the through-thickness modulus of a specimen further comprises determining the velocity of the first low-frequency ultrasonic wave through the specimen; determining the velocity of the first high-frequency ultrasonic wave through the specimen; determining the velocity of the second high-frequency ultrasonic wave through the specimen; determining the elastic constant corresponding to each low-frequency and high-frequency ultrasonic velocity; and calculating the through-thickness modulus of the specimen from the determined values.

According to another embodiment of the invention, a method for performing nondestructive evaluation of a specimen comprises: coupling a first ultrasonic wave transducer to a first contact point of a specimen to be tested; coupling a second ultrasonic wave transducer to a second contact point of the specimen at a predetermined distance from the first ultrasonic longitudinal wave transducer; transmitting a wave from the first ultrasonic wave transducer into the specimen; and receiving the wave by the second ultrasonic wave transducer, wherein the first ultrasonic wave transducer is configured to transmit a wave into the specimen, and the second ultrasonic wave transducer is configured to receive the wave from the first ultrasonic wave transducer; and inserting a delay line between at least one of the first ultrasonic wave transducer and the first contact point and the second ultrasonic wave transducer and the second contact point.

This arrangement provides particular advantages, including that the specimen to be tested or measured may be placed into an oven for testing. This permits the material to be tested at a particular temperature, and also eliminates the possibility of contamination of the specimen with a liquid or gel couplant.

According to a further embodiment of the invention, the method for performing nondestructive evaluation of a specimen further comprises operating the first ultrasonic wave transducer and the second ultrasonic wave transducer at or below 0.5 MHz (500 kHz).

This arrangement may ensure that the modulus measurement stays in the low frequency asymptote region of the lowest symmetric mode for an in-plane modulus evaluation on a thin specimen. The use of a longitudinal wave contact method on the same side of a thin specimen may induce the lowest symmetric mode of a Lamb wave, which makes it possible to perform nondestructive evaluation of specimens. The lowest symmetric mode is determined based on Lamb's guided wave theory. A Lamb wave occurs when the thickness of a plate is smaller than the ultrasonic wavelength of a plate. The term symmetric means the displacement or vibration of the Lamb wave is symmetric with respect to a plate. In Lamb waves, multiple modes could exist. The mode at the lowest frequency is usually called the lowest or fundamental mode.

According to another embodiment of the invention, the method for performing nondestructive evaluation of a specimen further comprises: inserting the specimen into an oven, wherein the first ultrasonic wave transducer and the second ultrasonic wave transducer are located outside the oven, and the delay lines couple the first ultrasonic wave transducer and the second ultrasonic wave transducer to the specimen.

This arrangement provides particular advantages, including that the specimen to be tested or measured may be placed into an oven for testing. This permits the material to be tested at a particular temperature, and also eliminates the possibility of contamination of the specimen with a liquid or gel couplant.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

Figure 1:
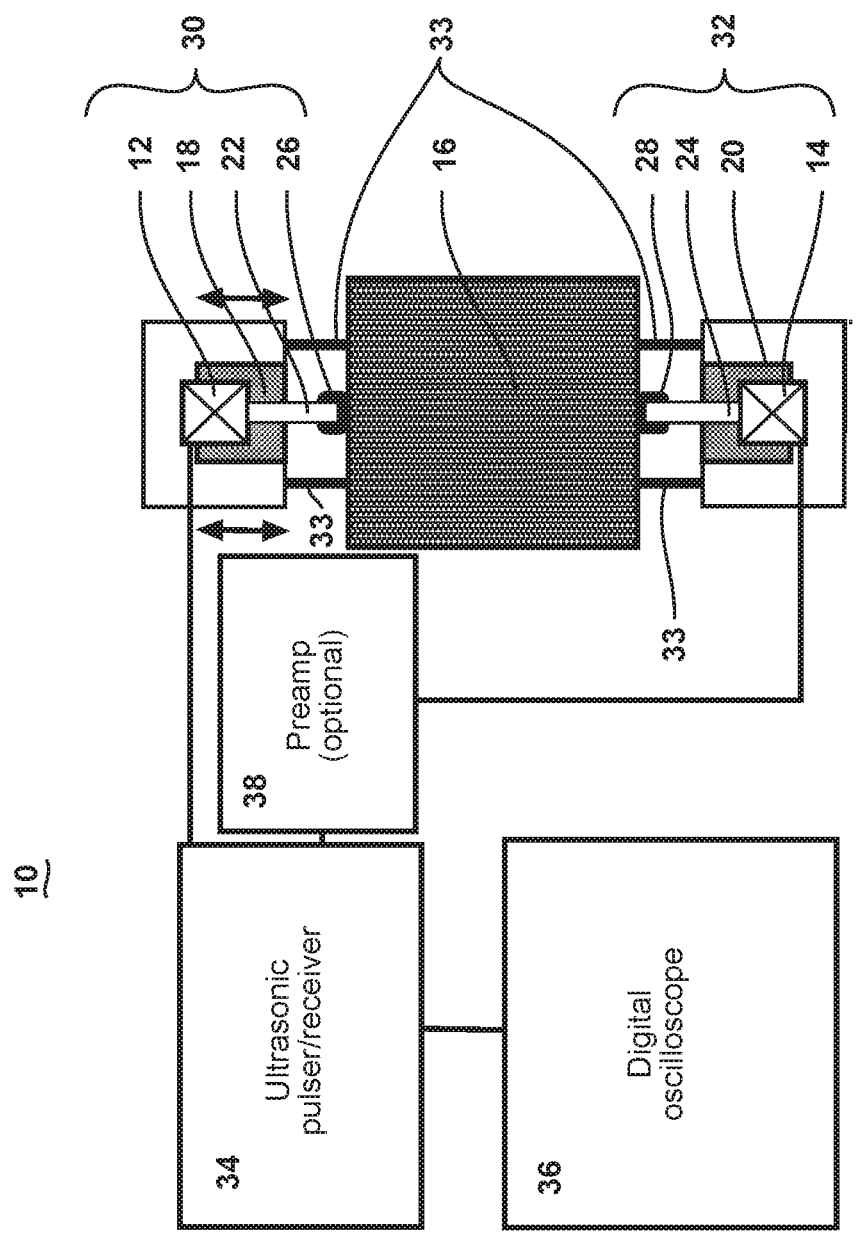
FIG. 1 depicts an apparatus for performing nondestructive evaluation of a specimen with ultrasound transducers in dry-contact with the specimen and using one or more delay lines, according to the invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

The purpose of this invention is to provide an easy and versatile nondestructive apparatus and method to monitor the through-thickness modulus (Young's modulus at the through-thickness direction) of a specimen, e.g. a thin composite plate, using a dry contact low frequency ultrasonic guided wave approach, such as with a delay line between the transducers and the specimen.

In one embodiment of this invention, a small diameter delay line may be attached to a transducer through a custom-made delay line fixture for passing low frequency guided waves through the delay line and into a specimen, e.g. a thin composite. At least three advantages have been found so far using this new approach: (a) the thin delay line approach is robust and exhibits less wear and tear than with a membrane for dry contact; (b) this approach exhibits increased spatial resolution; and (c) delay line dry contact approach enables monitoring of the modulus at elevated temperatures, e.g. when the specimen is in an oven.

In addition, this invention has three areas which are unique as compared to the prior art: (i) it is based the lowest order symmetric mode ultrasonic guided waves; (ii) generation and detection of the guided waves is in dry contact; and (iii) the in-plane modulus of a material may be easily assessed based on the velocity of this mode.

Regarding (i) above, most ultrasonic guided wave processes on are focused on higher order modes in which many different modes co-exist. The great number of simultaneous modes make it difficult to monitor small changes in materials using these higher order modes. However, the lowest order mode such as is employed in this invention exists in a region where only few modes are present. Therefore, it is much easier to identify any changes and to monitor variations in materials using the lowest order mode. Furthermore, in this invention a non-dispersive region of the lowest mode was selected for the modulus assessment. The term "symmetric" means the vibration is symmetric or mirrored with respect to a specimen. The term "lowest" is used because there are multiple higher modes at higher frequencies. This approach greatly reduces the need for using advanced tone burst equipment for a velocity measurement. Instead, a typical ultrasonic pulser/receiver may be used for a velocity measurement.

Regarding (ii) above, this invention also has the additional novelty of a dry-contact arrangement in the generation and detection of guided waves. Dry-contact may be made possible by using a delay-line, e.g. a waveguide, between one or both of the ultrasonic transducers and the specimen. Accordingly, ultrasound may be passed into a specimen without any typical, e.g. liquid or gel, ultrasonic couplant. This arrangement is quite distinct from the traditional processes and apparatuses for ultrasonic measurements using bulk waves or guided waves, which usually require ultrasonic gel or water immersion. The dry contact ultrasonic approach in this invention requires no ultrasonic couplant, i.e. no liquid, gel, or similar couplant, and thus reduces the risk of contaminating the materials.

Regarding (iii) above, based on this invention the in-plane modulus of a specimen may be monitored using this dry contact approach by monitoring the velocity of the guided ultrasonic wave generated in the specimen, e.g. composite plate. This in-plane modulus relates to material states in the specimen, and is often desirable at different stages of material processing including: raw materials, during processing, after manufacturing, in-between and after performance tests.

The inventive method and apparatus described herein is a dry contact ultrasonic approach based on low frequency guided wave technology. No traditional couplant is needed during a measurement. Thin composites with different amounts of porosity are able to be tested with the disclosed approach, and no couplant residue or contamination remains on the specimens after testing. Certain CMCs are not useful for many purposes if the porosity is too high. Advantageously, the costs of modulus testing according to the disclosed approach are relatively low, and the time required for testing is short. This dry contact guided ultrasonic method may be used in testing materials at ambient temperatures as well as at elevated temperatures. Progress of densification or infiltration in composite specimens may also be monitored using this method. Composites with layers or gradients may also be measured. No similar methods and apparatuses are known.

In this method, ultrasonic measurement of through-thickness (perpendicular to the layer of fibers in the specimen) modulus may involve: (1) low frequency ultrasonic measurement and procedure, (2) high frequency ultrasonic measurements; and (3) through-thickness modulus evaluation.

In order to perform low-frequency ultrasonic measurements, the disclosed apparatus (see FIG. 1) may comprise the following components: a pair of low-frequency longitudinal wave ultrasonic transducers for the generation and detection of guided waves in a specimen, e.g. a thin composite panel; a delay line may be attached to each transducer for delivering ultrasonic waves to and from the transducers; an assembly (delay line fixture, see FIG. 2) which holds both each transducer and its delay line together; a fixture which holds the transducer assemblies; an adjustable guide which includes two transducer assemblies with the ultrasonic sensing elements oriented face-to-face and which allows a specimen of nominal length to be inserted in between the transducer assemblies for an edge-to-edge inspection of the specimen, and calibration of the apparatus (see FIG. 3); an ultrasonic pulser-receiver for the generation and detection of ultrasound; and a digital oscilloscope which allows data acquisition of ultrasonic waveform on the display of the scope.

FIG. 1 illustrates a representative low-frequency setup 10, a pair of 200 kHz, 0.5" diameter longitudinal transducers 12, 14 (e.g. Olympus™ V1116) in custom fixtures 18, 20 in which the top fixture 18 can slide along a pair of guides 33 were applied to opposing edges of a CMC composite panel 16, through a metal, acrylic, or quartz delay line 22, 24 of small diameter (0.2" to 0.08"). To maintain functionality in the low frequency region through a delay line 22, 24, the product of frequency (in MHz) and thickness of the composite (in mm) should be kept around or less than 0.5 MHz*mm. The low-frequency measurement should also be maintained in the principal direction of a composite (i.e., 0° or 90° of fiber direction of a cross-ply composite). A membrane 26, 28 may be placed between the transducer 12, 14 and the delay line 22, 24. Optionally, a thin layer of viscous medium (e.g. honey) may be applied between the membrane and the delay line or the transducer to enhance the transmission and reception of ultrasonic signals across the membrane. Advantageously, no liquid or gel couplant is required between the specimen 16 and the delay lines 22, 24. The transducer assembly 30, 32 (which may comprise a transducer, delay line fixture, and a delay line) may be part of an additional fixture 33 which can slide up and down for inspecting specimens of different sizes. The specimen 16 may be held below the fixture 33 which includes the transducer assemblies 30, 32 which may include a nominal weight. The nominal weight of the fixture places a small dead weight on the specimen. The benefit of using a constant weight, instead of holding a transducer by hand, is to produce more repeatable results.

For optimized transmission of ultrasound through the specimen 16, the specimen 16 may be centered on each transducer 12, 14. A broadband ultrasonic pulser/receiver 34 (e.g. Olympus™ 5072PR) may be used for the generation and reception of ultrasonic signals. Amplification of signals using a preamp 38 (e.g. Olympus™ ultrasonic preamp) is optional and not required. A digital oscilloscope 36 (e.g. Agilent 54622A, LeCroy 9350A, or 24MXs-B) capable of acquiring waveforms may be used for the acquisition of ultrasonic waveforms on the display of the oscilloscope. The benefit of using this setup is that it allows the user to sense variations in the specimen, e.g. if the specimen has gradient or multiple layers with different compositions.

Figure 2:
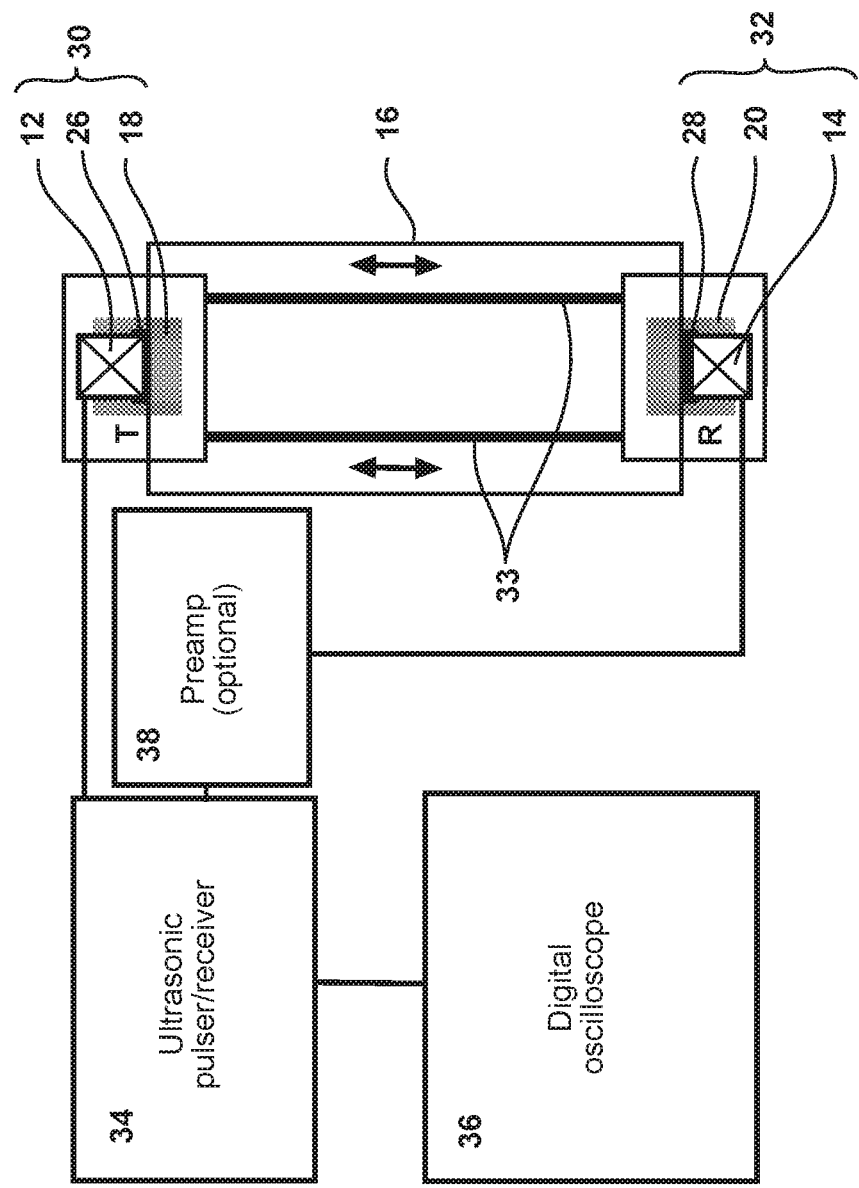
FIG. 2 depicts a specimen between a pair of dry-contact ultrasound transducers, according to the invention.

The embodiment of FIG. 2 employs a two-transducer setup in a through-transmission mode. The embodiment illustrated in FIG. 2 is very similar to that of FIG. 1 but without the small-diameter delay lines 22, 24 of FIG. 1. The top transducer assembly 30 and the bottom transducer assembly 32 comprise an ultrasonic transducer 12, 14, a custom fixture 18, 20 and a membrane dry couplant 26, 28, as in FIG. 1, but without a delay line. The disclosed apparatus provides great flexibility in non-destructively testing a wide variety of specimens, and without contaminating the specimen with couplant.

Figure 4:
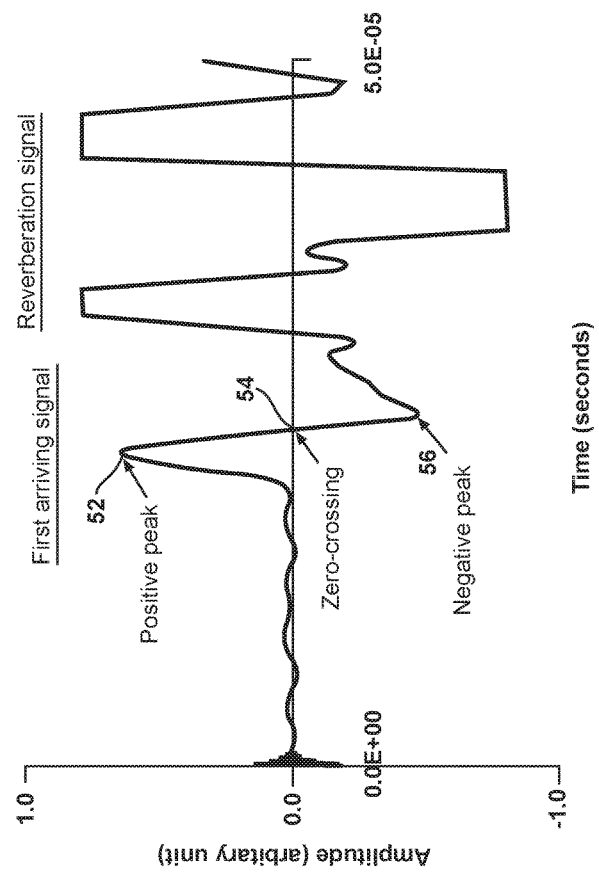
FIG. 4 illustrates an exemplary ultrasound signal, according to the invention.

In a typical low frequency test procedure, a calibration may be needed to be conducted first. This may be different from traditional ultrasonic velocity measurements where signals having multiple reflections (echoes or reverberation) within a specimen are clearly defined or multiple specimens of different dimensions of identical compositions are available. The ultrasonic signals of interest in this guided wave measurement are the first or the fastest signals which may be followed by several other signals (echoes) due to reverberation of ultrasound in the specimen, as illustrated in FIG. 4. Multiple reflections are often not clearly defined which is why the use of the first or fastest signals may provide an advantage. An unique way of the present invention as described in the following is to calculate the initial starting time position of ultrasonic signal based on this first signal.

Figure 3:
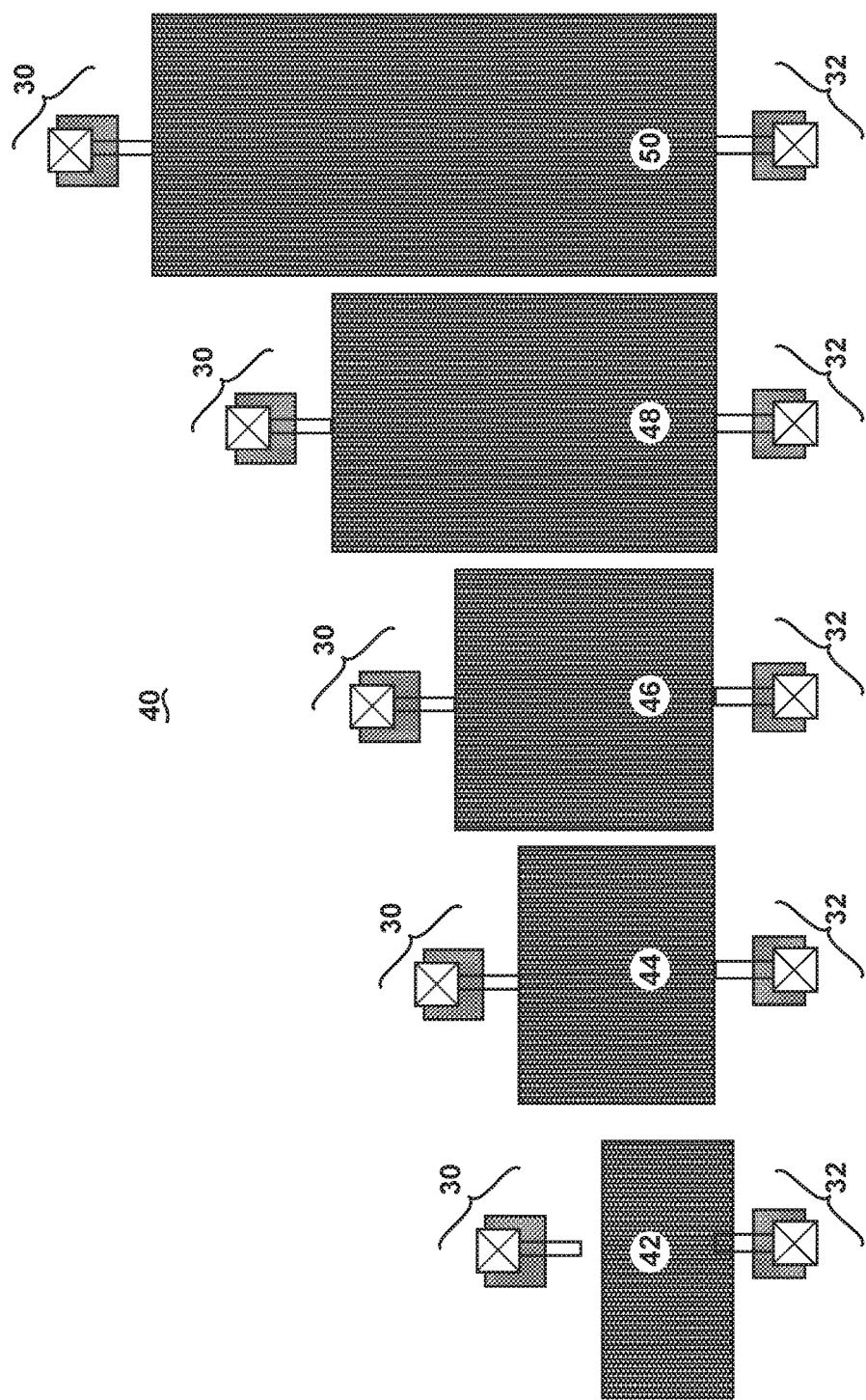
FIG. 3 depicts a calibration arrangement, according to the invention.

For a representative low frequency setup (see FIG. 3), calibration 40 is needed at the beginning of the test as described in the following. This test may start with ultrasonic measurements of a serial of thin plates (42, 44, 46, 48, 50) (e.g. 1 mm thick Al 2024-T3 and 60 mm wide) of different lengths (e.g. 30, 45, 60, 90,130 mm), as illustrated in FIG. 3. The ultrasonic signals of interest in this guided wave measurement are the first or the fastest signals which may be followed by several other signals due to reverberation (echoes) of ultrasound in the specimen, as illustrated in FIG. 4. In each of the fastest-arriving signals 52, the arrival time at the zero-crossing 54 prior to a peak 56 is be recorded. This zero-crossing approach may provide better time-definition or time-resolution than by using the peak of the signal. This is because, when expanded in the time domain, the peak signal may be spread out in a plateau, without giving a sharp arrival time as it may in its zero-crossing. Regarding the determination of the zero-crossing, after finding the fastest-arriving signals 52 (i.e., the earliest peak in a waveform), the zero-crossing next to a peak may be located by observing the switch of the sign in amplitude (i.e. from negative to positive or positive to negative). Mathematically, this zero-crossing 54 may be derived in two simple steps (i) calculate the product of amplitude in two adjacent points 52, 56 for each point in a waveform, and (ii) the zero-crossing is the point where the product has the lowest value (i.e. either negative or zero while the rest of them is positive).

After acquiring the waveforms for each length, the arrival time of the zero-crossing before the peak is recorded. A plot of the length is made with the arrival time of the zero-crossing arrival time of the signal. Afterwards, a linear best fit may be made based on the data acquired (see FIG. 5). The intercept of the best fit line on the time axis might not be at the origin of the plot. This may be due to the transducers having a wear plate on their front, which may delay the initial signal and may smear the initial signal. This signal may be further delayed by the presence of the delay line. These factors may make estimating the initial starting time difficult. Therefore, in the specimen test as described in the following, this intercept may be subtracted out of the zero-crossing from the first arrival signal. By using this intercept method, the time-of-flight in a specimen without multiple specimens or reflections may be accurately estimated.

Figure 5:
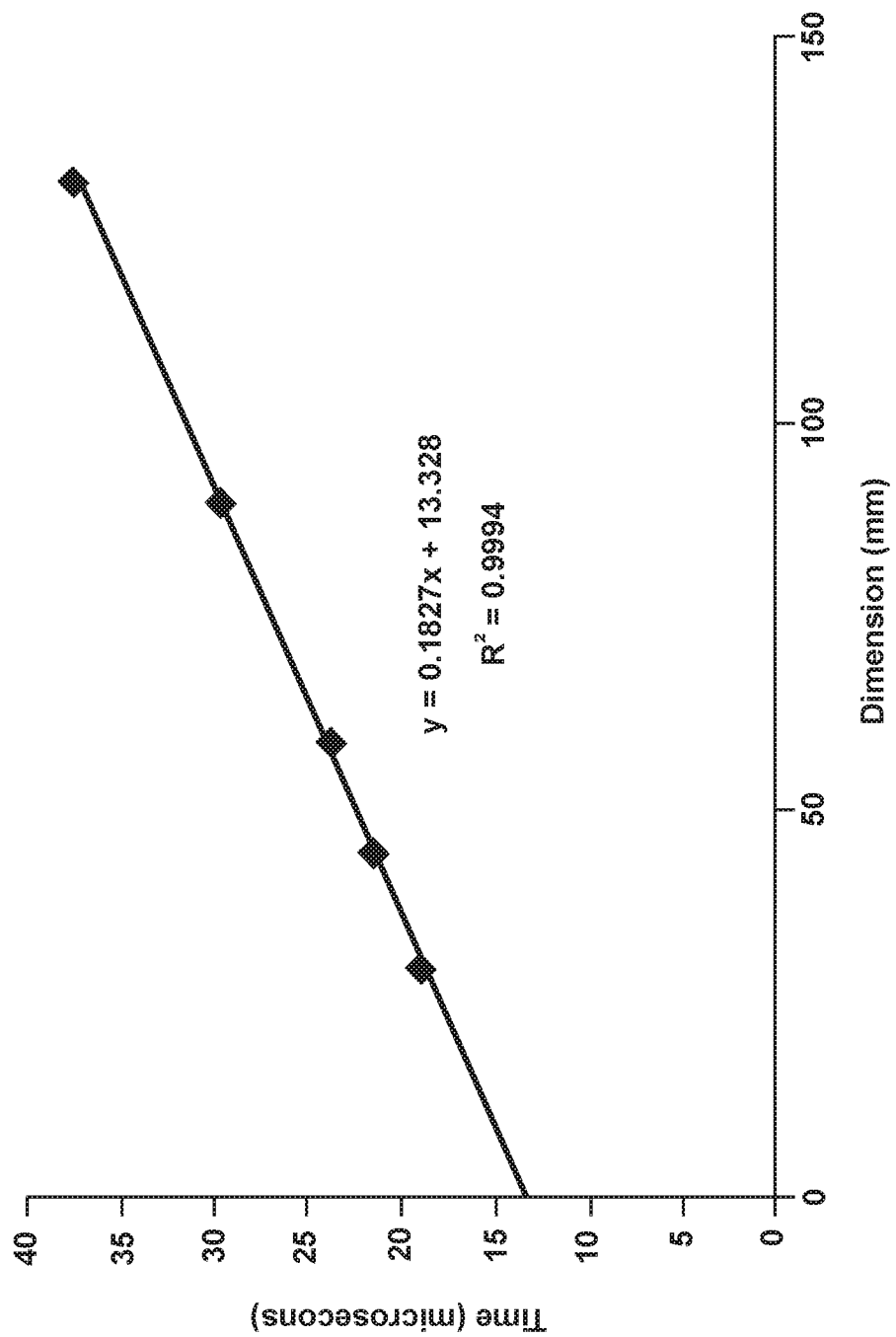
FIG. 5 illustrates the relationship between calibration dimensions and time of flight of an ultrasound waveform, according to the invention.

FIG. 5 explains that y=0.1827x+13.328 and $R^2$=0.9994. This is a linear best-fit of the data, which is also known as a linear trendline. The formula shown on FIG. 5 represents a line (i.e., y=mx+b, with m as the slope, and b as the intercept at the y-axis). The intercept is defined as the starting point of the ultrasonic signal from one end of the specimen (i.e., 13.328 microseconds). Therefore, one signal is needed to estimate the time-of-flight or velocity of ultrasound in a specimen. This is a unique approach. Others are using multiple specimens of different lengths or multiple reflections within a single specimen to calculate the velocity. In the present invention, by using this intercept approach, only one signal in one specimen is needed to evaluate the velocity.

With this calibration, we can then use only one ultrasonic signal in the specimen to estimate the velocity in the specimen while using the intercept at the beginning of the signal. For example, in FIG. 5, this is 13.328 microseconds. The $R^2$ or R-squared value, which ranges from 1.000 to 0.000, is an indicator that shows the scattering of data. The higher the R-squared value, the smaller the scattering of data around a line. In this case, our $R^2$ is 0.9994 which shows that our data follow a line very well with almost no scattering.

In a typical low-frequency test procedure, the next step may be a specimen test. During the specimen test, the same zero-crossing prior to a peak as calibrated should be recorded. The length of the specimen (in the ultrasonic test direction) should be measured e.g. with a pair of calipers. To prevent a skew or distortion of the ultrasonic signal, the measurement should be conducted in the principal direction of a composite. For example, the direction should be either along or across the fibers or [0°] or [90°] but not in between such as [45°]. For a [0°/90°] composite, measurement in both orientations may be made. The arrival time of each orientation is recorded along with the length of each orientation in order to support the determination of the modulus later.

High-frequency ultrasonic measurements may have a similar experimental setup and calibration requirement to those of the low-frequency measurements described above. The major difference is in the transducers and couplant which are used. For high-frequency measurements, a pair of high-frequency longitudinal wave ultrasonic transducers (15 MHz or above) are used for the generation and detection of bulk waves in a thin composite panel. A thin film of water may be the only couplant needed for coupling the high-frequency transducers to the specimen. Two distinct high-frequency measurements may be performed on the specimen: (i) in-plane (in the width direction, parallel to the layer of fibers in the specimen) and (ii) out-of-plane (in the through-thickness direction, perpendicular to the layer of fibers in the specimen).

Figure 6:
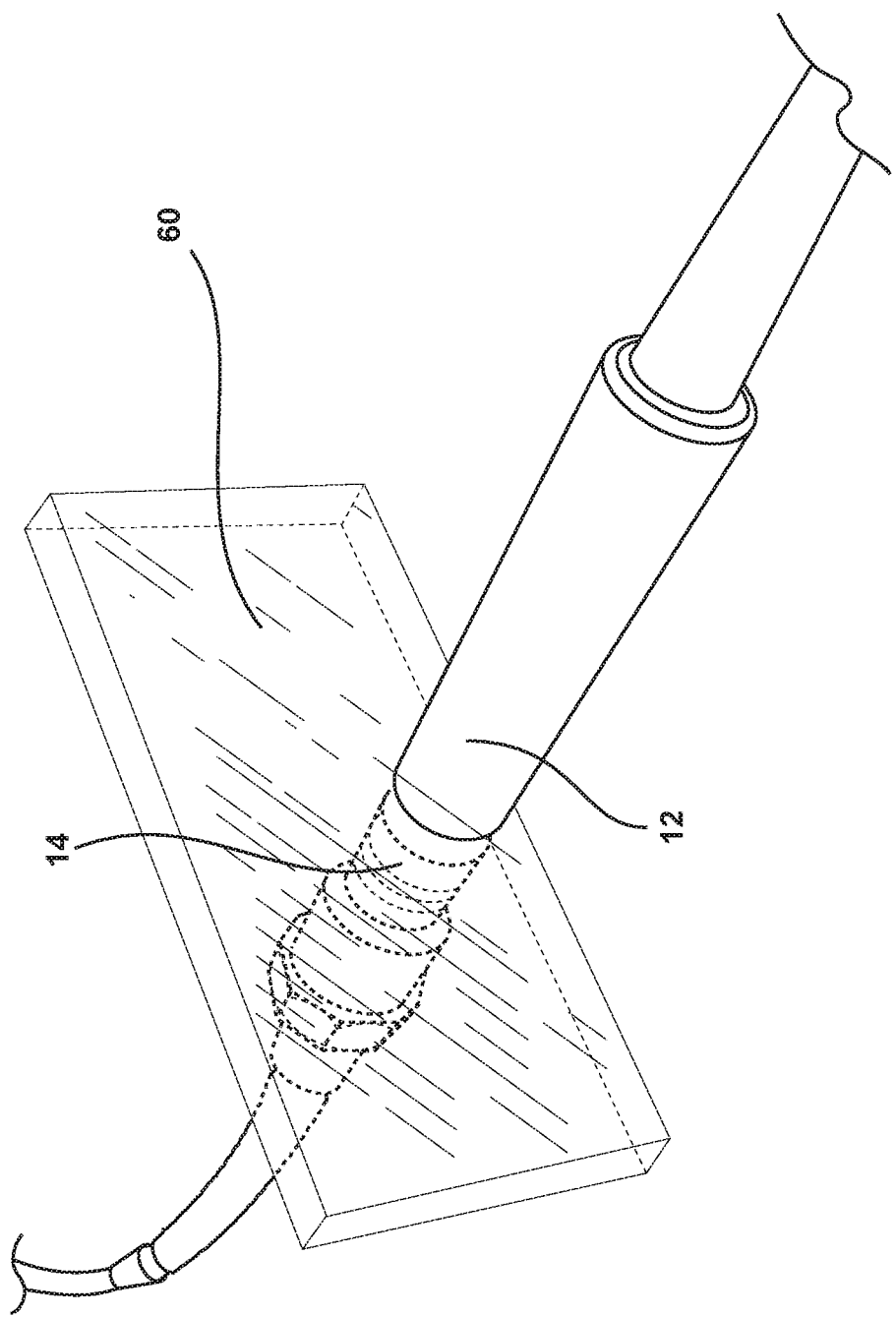
FIG. 6 depicts through-thickness calibration with two high-frequency longitudinal wave transducers and a calibration plate of known dimensions, according to the invention.
Figure 7:
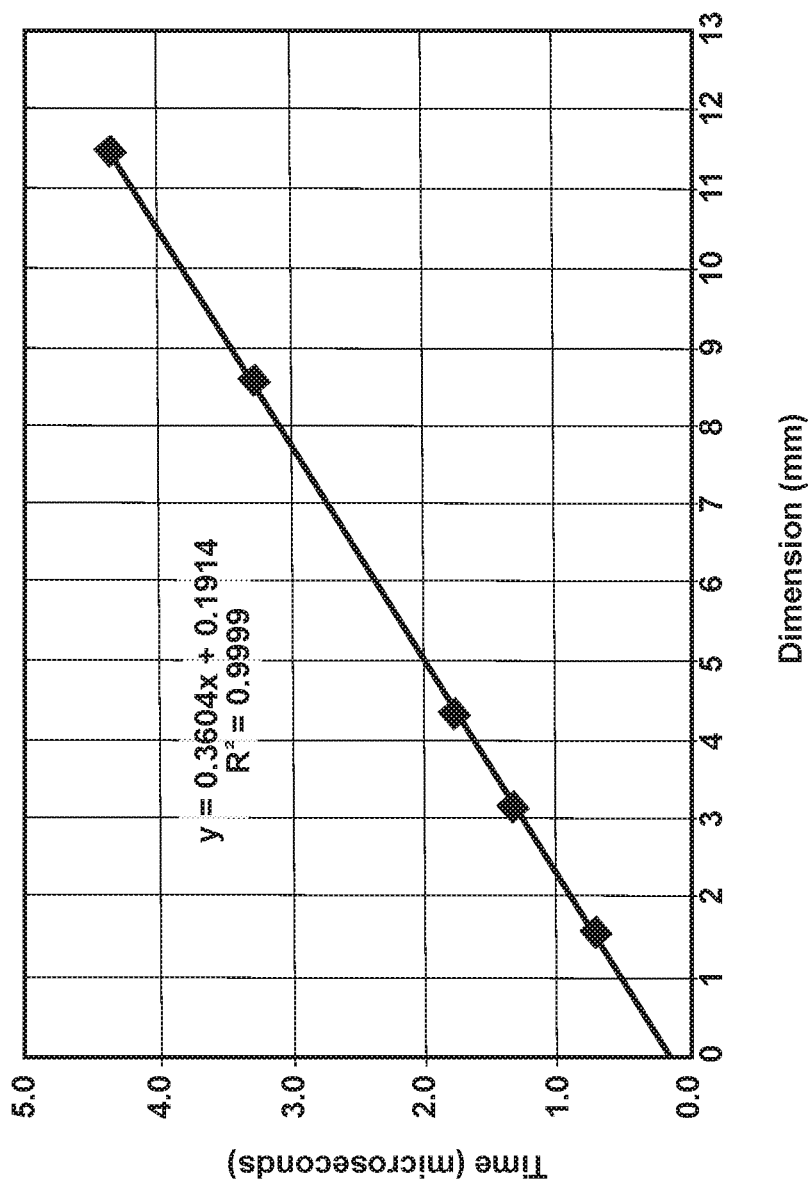
FIG. 7 illustrates the relationship between time of flight of ultrasonic signals and the thicknesses of a plurality of calibration plates, according to the invention.
Figure 8:
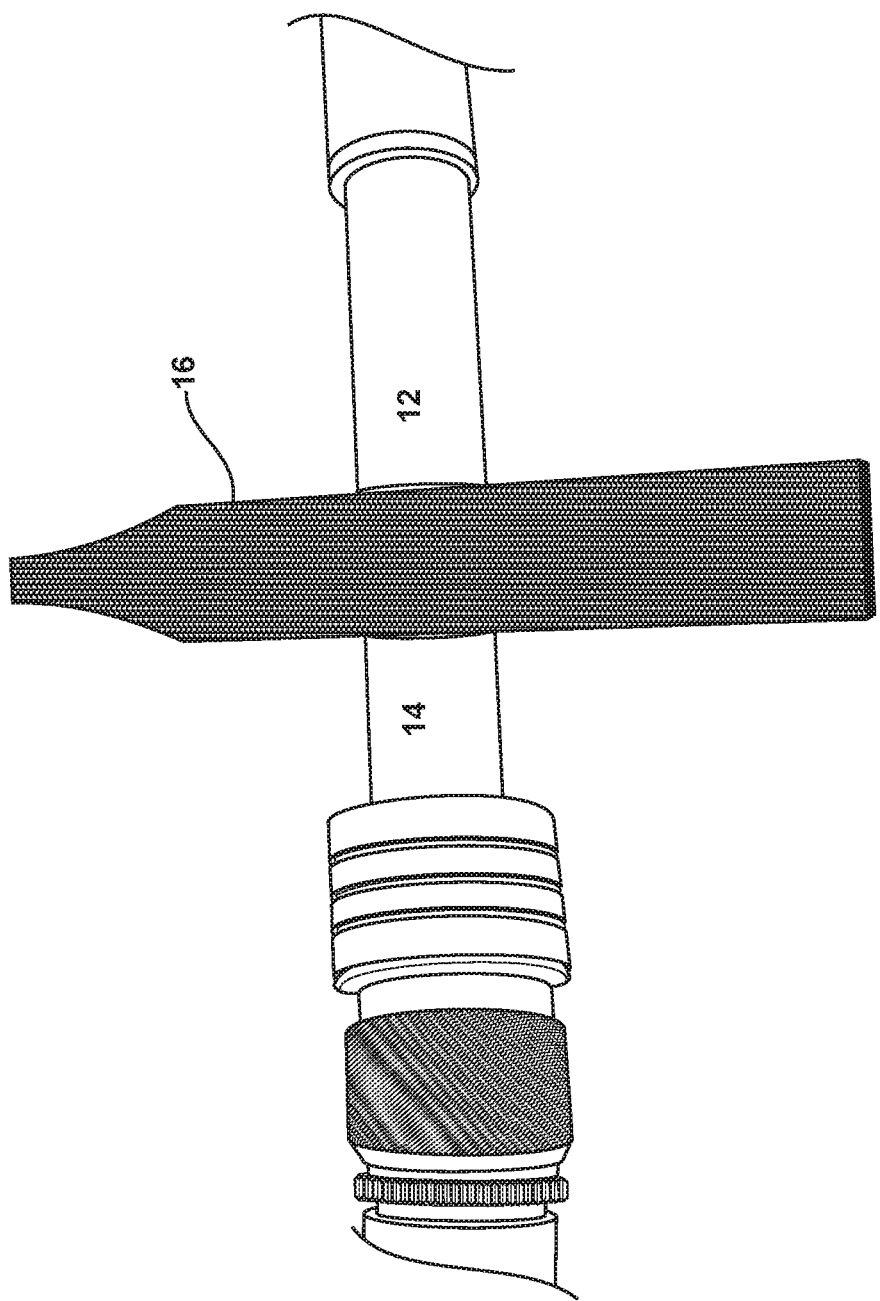
FIG. 8 depicts the pair of high frequency longitudinal wave transducers mounted on a specimen in order to determine the in-plane velocity of ultrasonic waves, according to the invention.

The first high-frequency ultrasonic measurements in the in-plane direction (width of the specimen, corresponding to the direction of the fibers) may also require a similar calibration as that of low-frequency measurements. The calibration may be based on a series of Plexiglas™ plates 60 of different known thicknesses (see FIG. 6). As above with regard to the low-frequency measurements, the time of the first arrival signal is plotted against the thickness (see FIG. 7). A linear best fit of the data may be plotted, as illustrated in FIG. 7. The intercept of this line on the time axis may be recorded to yield the offset time. This offset time may be subtracted from the time acquired during ultrasound measurements on the specimen 16 (see FIG. 8).

Figure 9:
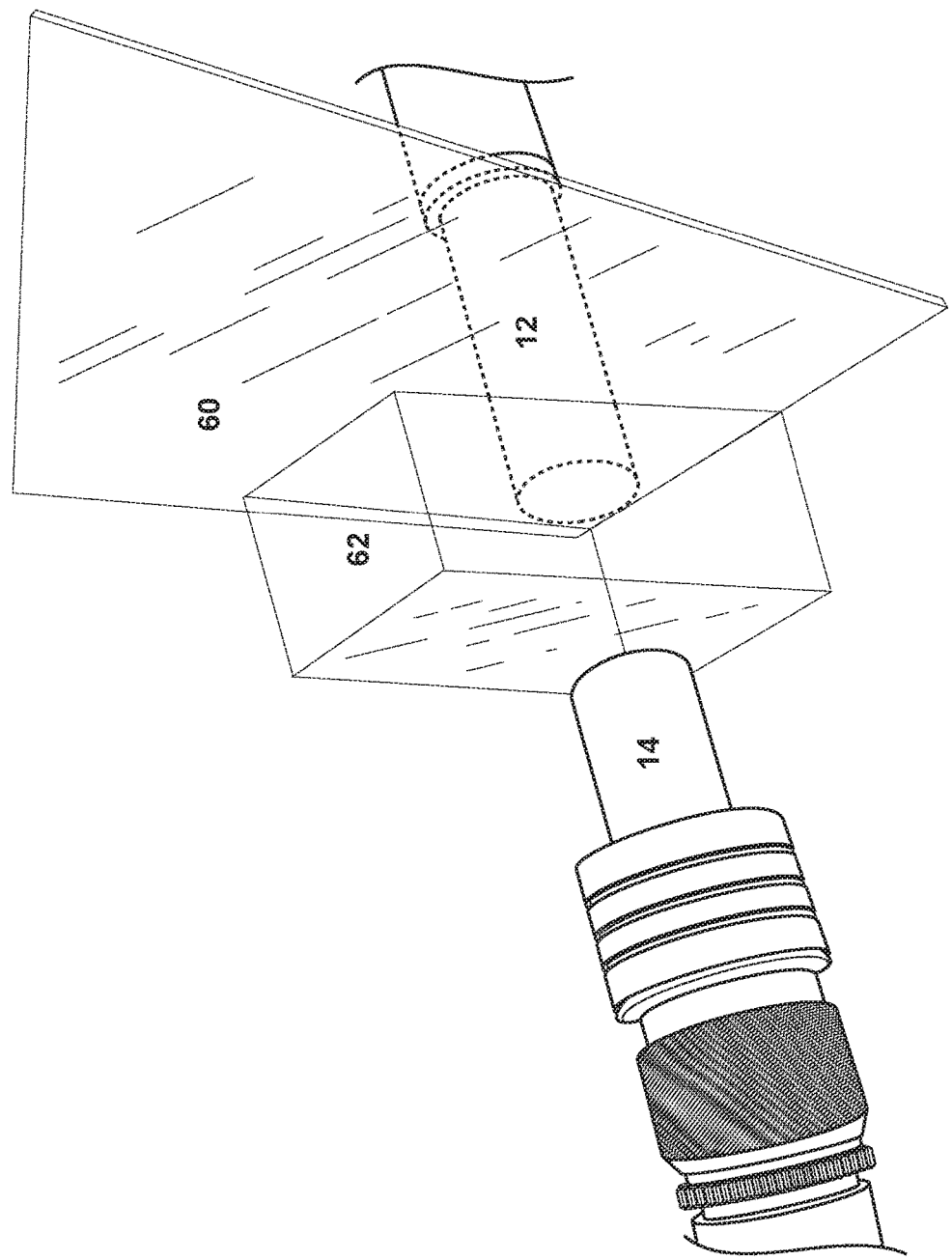
FIG. 9 depicts a glass plate utilized as a delay line between two high-frequency longitudinal wave transducers, according to the invention.
Figure 10:
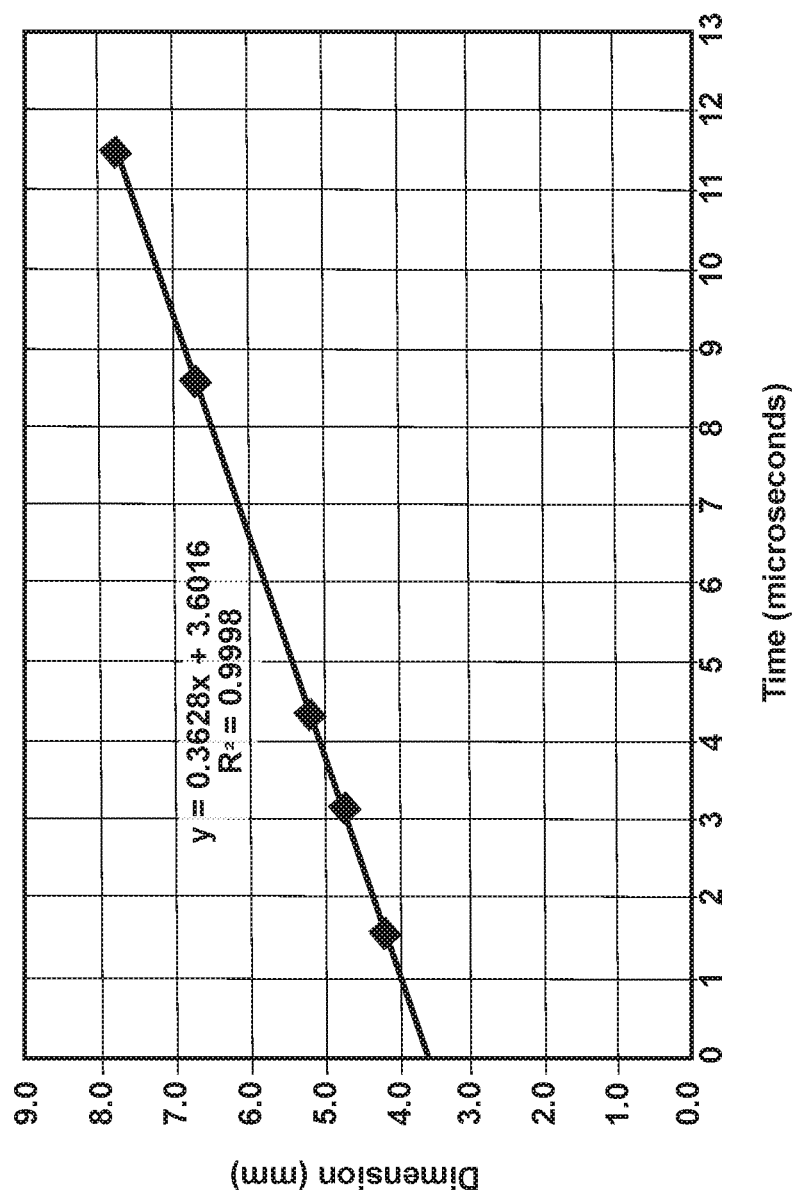
FIG. 10 illustrates calibration results depicting the time required to receive the first ultrasonic waves for the relationship corresponding to the thickness of Plexiglas calibration plates having known dimensions and a glass plate delay line, according to the invention.
Figure 11:
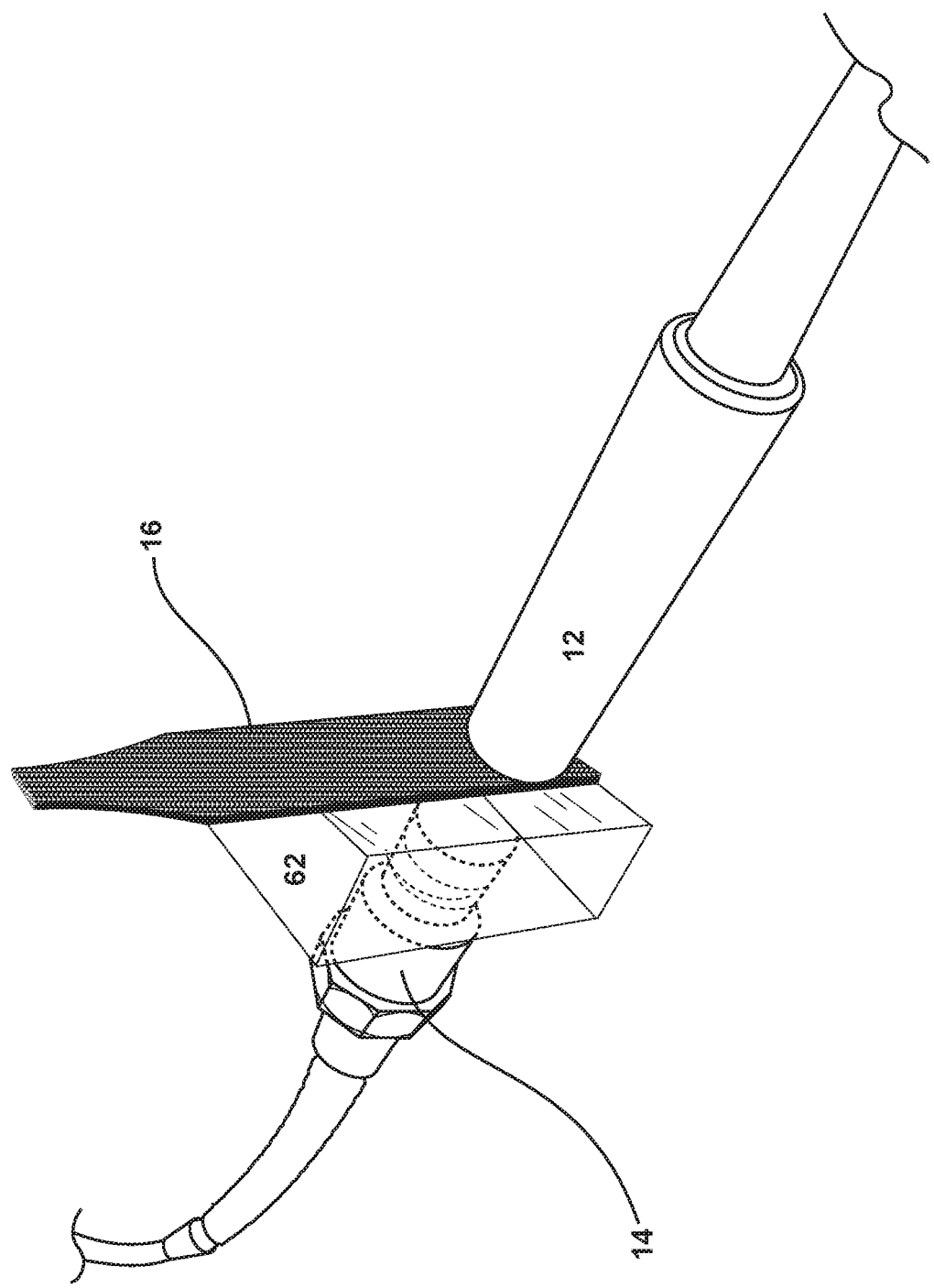
FIG. 11 depicts through-thickness high frequency ultrasonic measurements of a specimen with a Plexiglas™ block delay line, according to the invention

The second high-frequency ultrasonic measurement in the out-of-plane (thickness) direction may also require a similar calibration as that of the low-frequency measurement described above. In addition to the Plexiglas plates 60 of different thicknesses, a thick (¾-inch or 19 mm) glass plate 62 may also be added as a delay line (see FIG. 9). The delay line may be may be employed in order to offset the arriving (return or echo) signal away from the initial signals. The time of the first arrival signal may be plotted against the thickness of the specimen 16, as illustrated in FIG. 10. A linear best fit of the data may be plotted (see FIG. 10). The intercept of this line on the time axis may be recorded to derive an offset time. During the specimen measurement (see FIG. 11), the thick glass plate 62 may remain with the setup. The derived offset time may then be subtracted from the time acquired from the specimen 16. The following figure illustrates this test procedure:

In a typical test procedure, the third step may be a calculation of the through-thickness modulus (which may be determined from the test depicted in FIG. 10). For this through-thickness evaluation, the Poisson's ratio and the density of the material are also needed. The Poisson's ratio may be acquired by a separate test using mechanical means or by ultrasonic measurements. For a specimen 16, e.g., a CMC sample, with a smaller Poisson's ratio (i.e., about 0.2), the effect of the Poisson's ratio may not be significant. For example, an increase of the Poisson's ratio by 100% in the calculation may result in a 4% decrease (or 9 GPa reduction) of the in-plane modulus for a typical CMC material. For testing of materials in a rod form, the Poisson's ratio term may be taken out of the equation when calculating the in-plane modulus. Unlike the Poisson's ratio, the density has significant effect on the modulus estimate. A correct density determination or value is important for the modulus evaluation. Furthermore, if the modulus of a composite panel is known, the disclosed invention may also be used to evaluate local density variations in the panel.

The evaluation of the through-thickness modulus may be determined through the evaluation of elastic constants which may be estimated from the ultrasonic velocity measurements. For anisotropic composites with orthotropic symmetry, according to the classical mechanics, there are nine independent elastic constants. For cross-ply composites, the through-thickness modulus is dependent on four independent elastic constants because of the symmetry in the 0-deg and 90-deg directions. Three of the constants may be solved using the three ultrasonic measurements described above, while the fourth elastic constant may be solved using additional information from the Poisson's ratio. Thus, the through-thickness modulus may be calculated through elastic constants $C_{11}$, $C_{33}$, $C_{13}$ and $C_{12}$. The equations are presented below. These elastic constants may be calculated based on the ultrasonic velocities, the Poisson's ratio ($\upsilon$), and the density ($\varphi$) of the material. For example: elastic constant $C_{11}$ may be calculated via the high-frequency ultrasonic velocity $V_{hf1}$ at the in-plane direction. Elastic constant $C_{33}$ may be calculated via high frequency ultrasonic velocity $V_{hf2}$ at the out-of-plane direction. Elastic constant $C_{13}$ can be calculated via low frequency ultrasonic velocity $V_{lf}$ at the in-plane direction. Elastic constant $C_{12}$ may be calculated via these three elastic constants with additional information from the Poisson's ratio for the specimen. Once these four elastic constants are calculated, the through-thickness modulus ($E_3$) may be evaluated/determined using the following equations:

$$E_3 = \frac{C_{11}^2 C_{33} + 2C_{13}^2 C_{12} - 2C_{11}C_{13}^2 - C_{33}C_{12}^2}{C_{11}^2 - C_{12}^2} \text{ where}$$

$$C_{11} = \rho V_{lf1}^2$$
$$C_{33} = \rho V_{lf2}^2$$
$$C_{13} = \sqrt{C_{33}(C_{11} - \rho V_{lf}^2)}$$
$$C_{12} = V_{12}\left(C_{11} - \frac{C_{13}^2}{C_{33}}\right) + \frac{C_{13}^2}{C_{33}}$$

This invention has numerous applications, including (a) modeling, (b) material processing, and (c) raw material screen. With regard to modeling, the through-thickness modulus estimated ultrasonically may provide critical input parameters needed for FEM (Finite Element Method) modeling. Regarding material processing, the in-plane modulus estimated ultrasonically may provide important feedback on the degree of infiltration processing which may be needed to densify a composite during material processing. Regarding raw material screening, the through-thickness modulus estimated ultrasonically may provide information regarding the material states of any materials received for material processing. For example, the presence of porosity or thermal damage may also reduce the values of apparent in-plane modulus.

This disclosure presents several novel features: the through-thickness modulus of a thin composite may be determined nondestructively based on ultrasonic measurements; the disclosed ultrasonic evaluation of through-thickness modulus method may be applied to both thin cross-ply composites with orthotropic symmetry as well as isotropic thin plates; the use of a calibration method to locate the starting point in the time domain based on the lowest symmetric mode of a guided wave; and the combined usage of multiple ultrasonic measurements of elastic constants in different directions for the evaluation of through-thickness modulus is a new concept.

Figure 12:
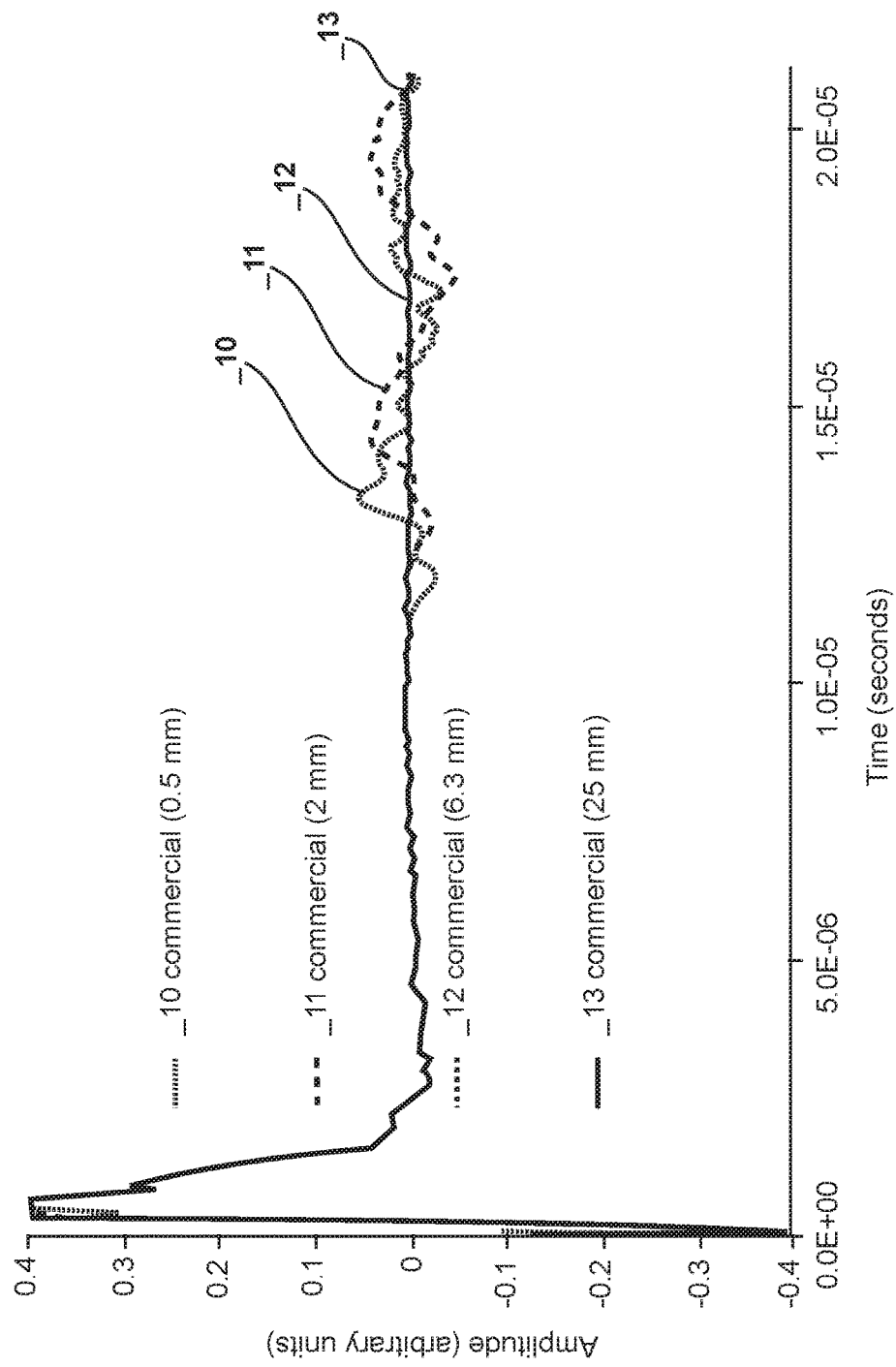
FIG. 12 illustrates ultrasonic signal sensitivity of commercially available NDE membrane materials, according to the invention.
Figure 13:
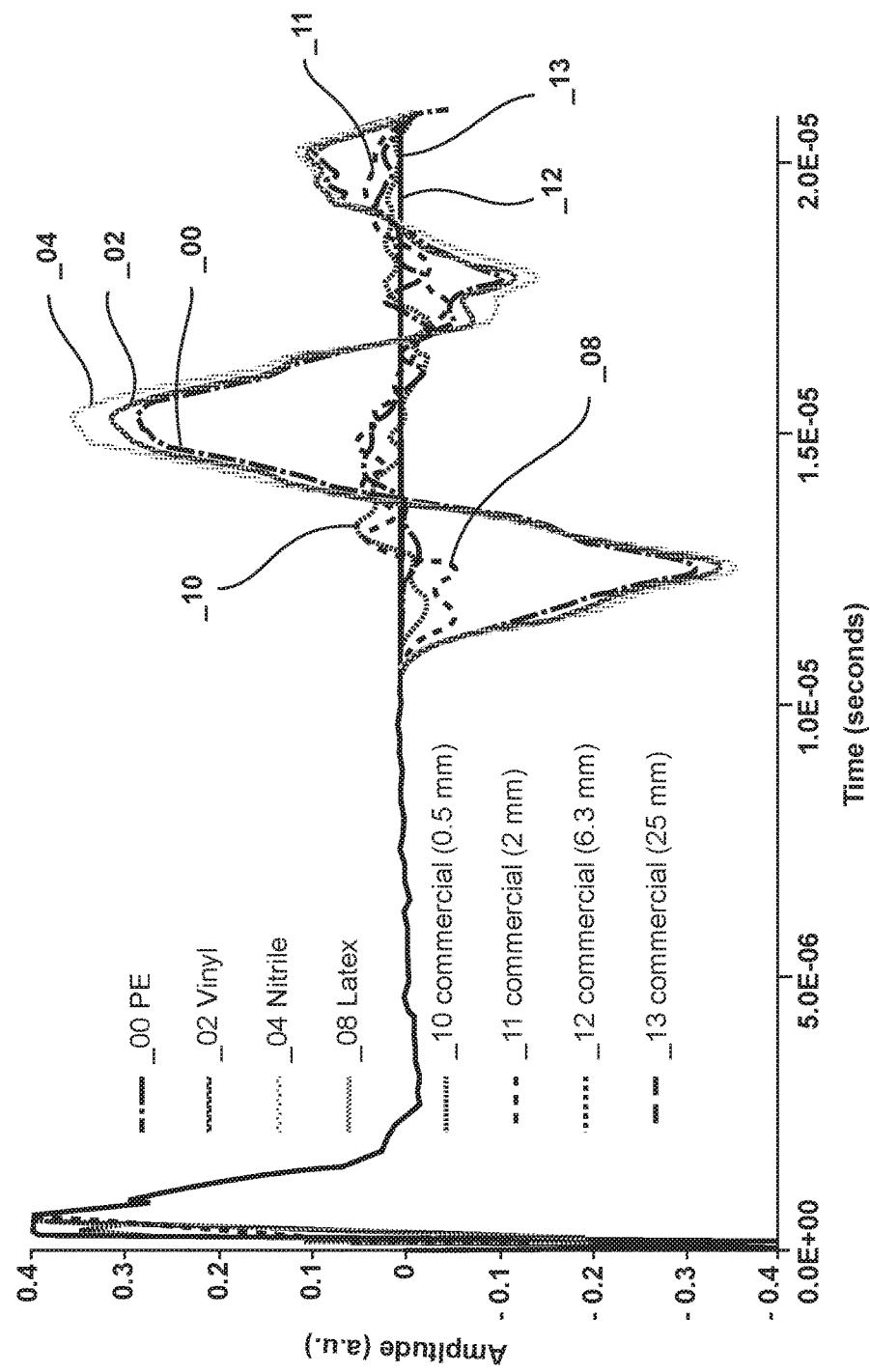
FIG. 13 illustrates ultrasonic signal sensitivity of nitrile, vinyl, and polyester (PE), according to the invention.
Figure 14:
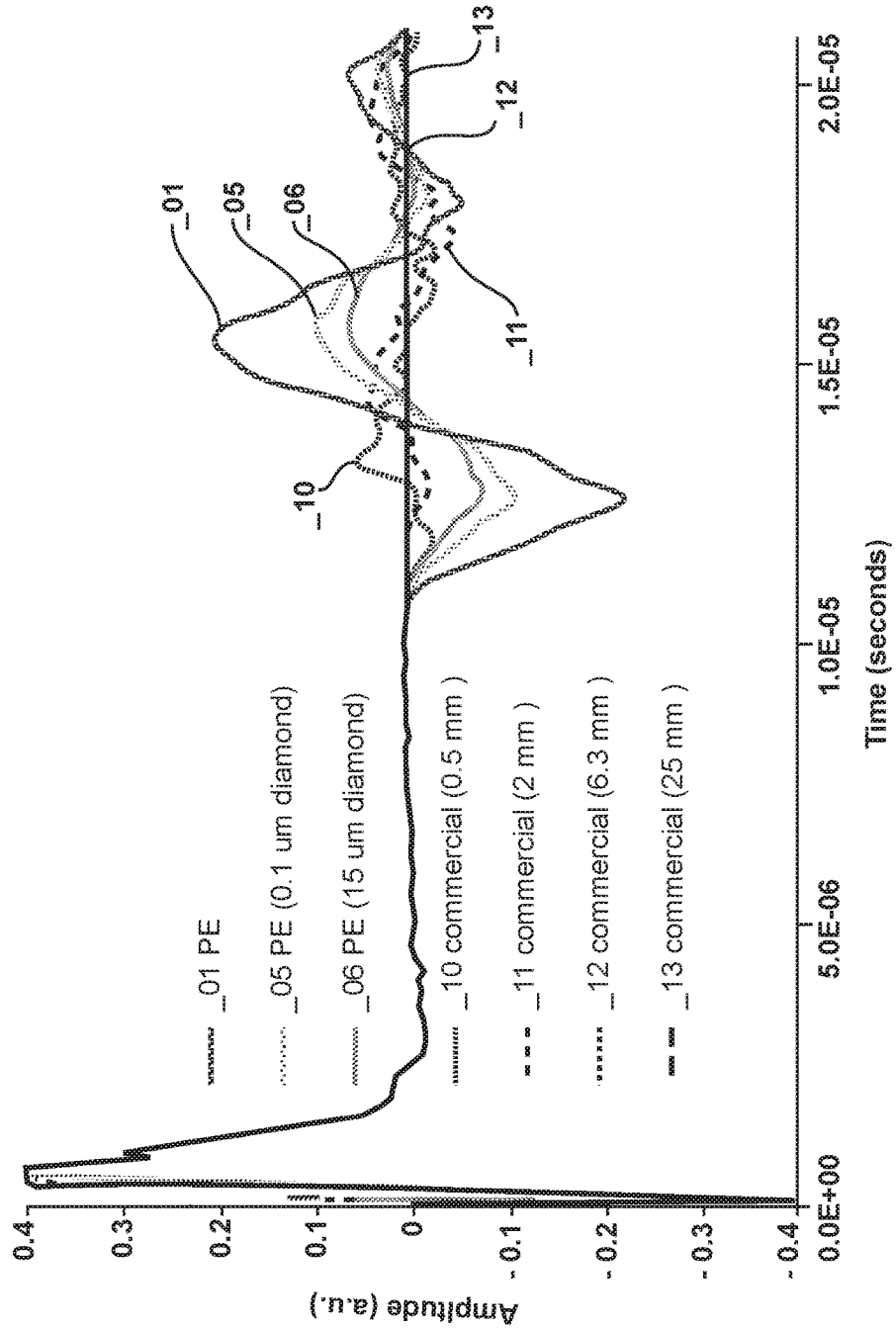
FIG. 14 illustrates ultrasonic signal sensitivity of PE with 0.1 micron diamond particles and PE with 15 micron diamond particles, according to the invention.
Figure 15:
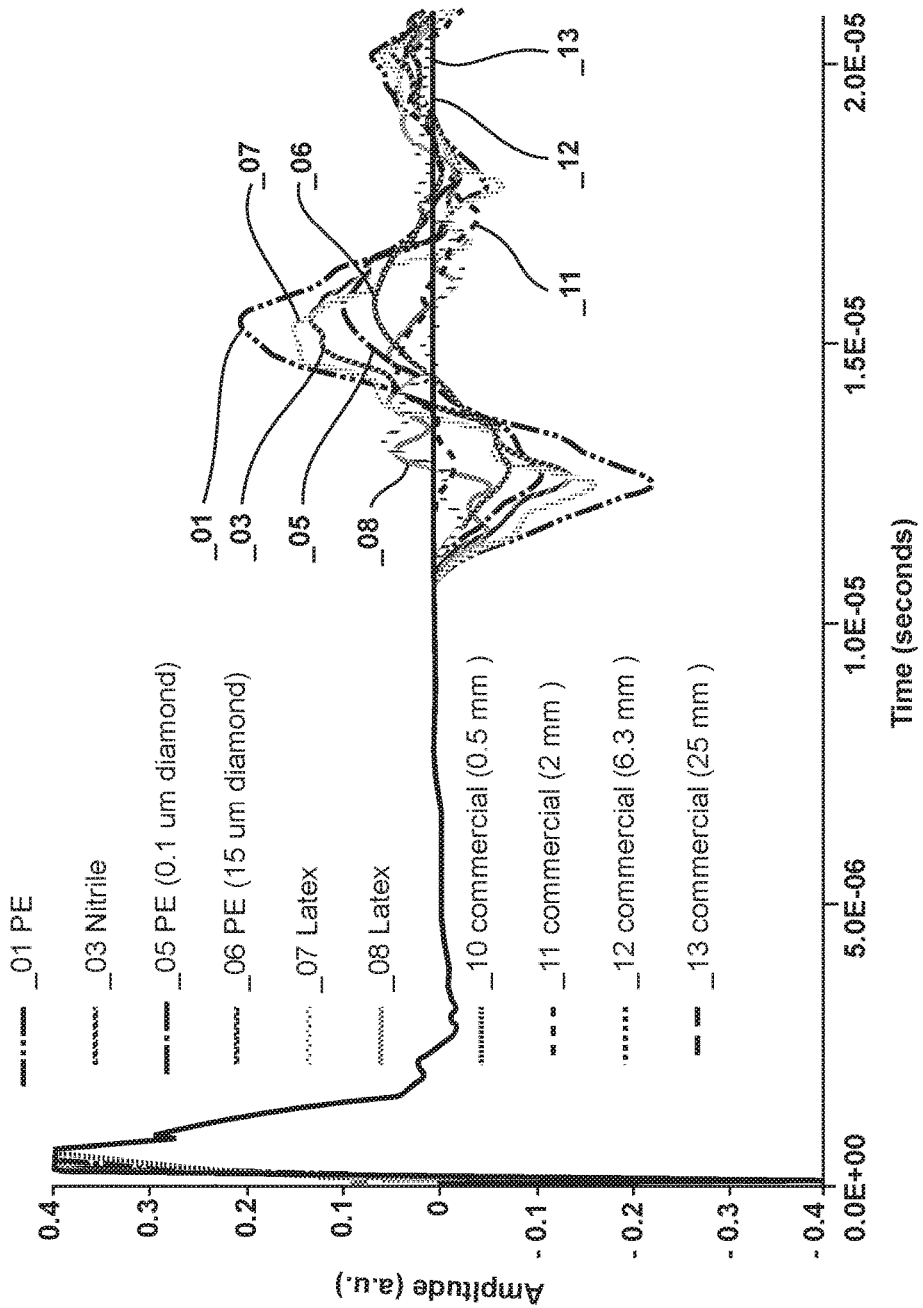
FIG. 15 illustrates ultrasonic signal sensitivity of latex, according to the invention.
Figure 16:
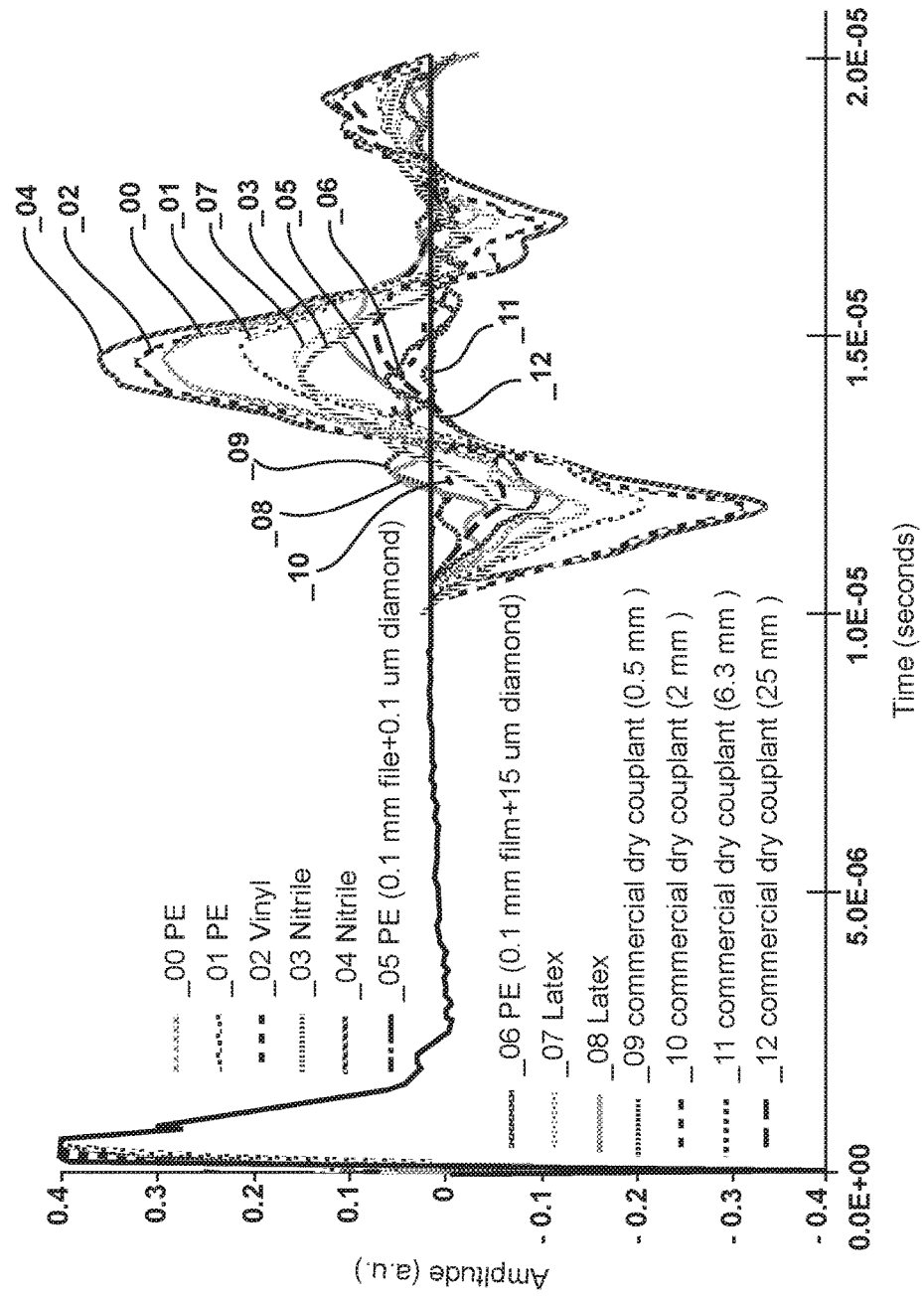
FIG. 16 illustrates ultrasonic signal sensitivity of commercially-available membrane materials, nitrile, vinyl, polyester, polyester with diamond particles, and latex, according to the invention.

FIGS. 12-16 illustrate the effect of particular membrane materials on the ultrasonic signal sensitivity, according to the disclosed invention and method. During the course of invention development, membrane materials with superior ultrasonic signal sensitivity were identified and the effects of their thickness observed. Based on signal sensitivity, four groups were examined (1) commercially available NDE membrane materials obtained from Olympus (FIG. 12); (2) nitrile, vinyl, and polyester (PE) (FIG. 13); (3) PE with 0.1 micron diamond particles and PE with 15 micron diamond particles (FIG. 14); (4) latex (FIG. 15). The signals were observed to decrease as the thickness increased. The results are compiled in FIG. 16, which shows that nitrile, vinyl, and polyester have significantly better sensitivity than commercially available membranes.

As is illustrated in FIG. 12, the commercially-available membranes are not nearly sensitive enough to couple ultrasonic energy into a specimen. The thick commercial dry couplant has an impedance similar to water and has a unique composition. On the other hand (FIGS. 13-15), polyethylene, vinyl, and nitrile membrane materials are optimal or preferable for use according to the present disclosure. In particular polyethylene membranes having a thickness of 0.05 mm to 0.15 mm, or vinyl membranes having a thickness of 0.05 mm to 0.15 mm, or nitrile membranes having a thickness of 0.05 mm to 0.15 mm. Although the thickness of these membranes may have some effect on the transmission of ultrasound therethrough, the material of the membrane also plays a part affecting the transmission of ultrasound through it. This is because the thickness of each of these membranes is relatively small as compared to the ultrasound wavelength (i.e., around 10 mm) through each membrane. For example, latex-type membranes produce much worse signals than do the nitrile-type of membranes. The material properties of the membrane, e.g. the modulus of elasticity and density, play a major role affecting the transmission of ultrasound through the membrane between a transducer and a specimen. In addition, the surface roughness or texture, caused by addition of diamond particles on PE membrane, may also affect the transmission of ultrasound through the membrane.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. An apparatus for performing non-destructive evaluation of the through-thickness modulus of a specimen comprises:
   a first low-frequency ultrasonic longitudinal wave transducer configured to be coupled to a first surface of a specimen to be tested with a first delay line, the specimen having a layer of fibers perpendicular to the first surface and the second surface;
   a second low-frequency ultrasonic longitudinal wave transducer configured to be coupled to a second surface of the specimen with a second delay line, the second contact point at a predetermined distance from the first contact point, the predetermined distance corresponding to the distance between the first surface and second surface, wherein the first low-frequency ultrasonic longitudinal wave transducer is configured to transmit a guided wave into the specimen in plane with layer of fibers, and the second low-frequency ultrasonic longitudinal wave transducer is configured to receive the guided wave from the first ultrasonic longitudinal wave transducer; and
   a first high-frequency longitudinal wave transducer and a second high-frequency longitudinal wave transducer configured to generate and receive both in-plane and out-of-plane ultrasonic signals in the specimen.

2. The apparatus for performing nondestructive evaluation of the through-thickness modulus of a specimen of claim 1, wherein the first low-frequency ultrasonic longitudinal wave transducer and the second ultrasonic longitudinal wave transducer are configured to operate at or below 0.5 MHz (500 kHz).

3. The apparatus for performing nondestructive evaluation of the through-thickness modulus of a specimen of claim 1, further comprising a dry couplant between the first and second low-frequency ultrasonic longitudinal wave transducers and the specimen.

4. The apparatus for performing nondestructive evaluation of the through-thickness modulus of a specimen of claim 3, wherein the dry couplant comprises a membrane between the first and second low-frequency ultrasonic longitudinal wave transducers and the specimen.

5. The apparatus for performing nondestructive evaluation of the through-thickness modulus of a specimen of claim 3, wherein the dry couplant is a nitrile rubber, vinyl, or polyester membrane.

6. The apparatus for performing nondestructive evaluation of the through-thickness modulus of a specimen of claim 1, wherein the first high-frequency ultrasonic longitudinal wave transducer and the second high-frequency ultrasonic longitudinal wave transducer are configured to operate at or above 15 MHz.

7. A method for performing nondestructive evaluation of the through-thickness modulus of a specimen comprises:
   coupling a first low-frequency ultrasonic wave transducer to a first surface of a specimen to be tested with a first delay line;
   coupling a second low-frequency ultrasonic wave transducer to a second surface of the specimen at a predetermined distance from the first low-frequency ultrasonic longitudinal wave transducer with a second delay line, the specimen having a layer of fibers oriented perpendicular to the first surface and the second surface, the predetermined distance corresponding to the distance between the first surface and the second surface;
   transmitting a wave from the first low-frequency ultrasonic wave transducer into the specimen at the first surface via the first delay line; and
   receiving the wave by the second low-frequency ultrasonic wave transducer at the second surface via the second delay line, wherein the first low-frequency ultrasonic wave transducer is configured to transmit a guided wave into the specimen, and the second low-frequency ultrasonic wave transducer is configured to receive the guided wave from the first low-frequency ultrasonic wave transducer; and
   coupling a first high-frequency longitudinal wave transducer at the first surface to transmit a first high-frequency ultrasonic wave into the specimen;
   coupling a second high-frequency longitudinal wave transducer at the second surface to receive the first high-frequency ultrasonic wave;
   coupling the first high-frequency longitudinal wave transducer at a third surface to transmit a second high-frequency ultrasonic wave into the specimen;
   coupling the second high-frequency longitudinal wave transducer at a fourth surface to receive the second high-frequency ultrasonic wave, the third surface and further surface being perpendicular to the first surface and second surface.

8. The method for performing nondestructive evaluation of the through-thickness modulus of a specimen of claim 7, further comprising:
   operating the first low-frequency ultrasonic wave transducer and the second low-frequency ultrasonic wave transducer at or below 0.5 MHz (500 kHz).

9. The method for performing nondestructive evaluation of the through-thickness modulus of a specimen of claim 7, further comprising:
   operating the first high-frequency ultrasonic wave transducer and the second high-frequency ultrasonic wave transducer at or above 15 MHz.

10. The method for performing nondestructive evaluation of the through-thickness modulus of a specimen of claim 7, further comprising:
   determining the velocity of the first low-frequency ultrasonic wave through the specimen;
   determining the velocity of the first high-frequency ultrasonic wave through the specimen;
   determining the velocity of the second high-frequency ultrasonic wave through the specimen;
   determining the elastic constant corresponding to each low-frequency and high-frequency ultrasonic velocity; and
   calculating the through-thickness modulus of the specimen.

\* \* \* \* \*